(12) United States Patent
Carmeli et al.

(10) Patent No.: US 8,624,227 B2
(45) Date of Patent: Jan. 7, 2014

(54) OPTOELECTRONIC DEVICE AND METHOD OF FABRICATING THE SAME

(75) Inventors: Chanoch Carmeli, Tel Aviv (IL); Yossi Rosenwaks, Hod-HaSharon (IL); Itai Carmeli, Tel-Aviv (IL); Ludmila Frolov, Rishon-LeZion (IL)

(73) Assignee: Ramot at Tel-Aviv University Ltd., Tel Aviv (IL)

( * ) Notice: Subject to any disclaimer, the term of this patent is extended or adjusted under 35 U.S.C. 154(b) by 693 days.

(21) Appl. No.: 12/310,283

(22) PCT Filed: Aug. 22, 2007

(86) PCT No.: PCT/IL2007/001046
§ 371 (c)(1),
(2), (4) Date: Sep. 15, 2010

(87) PCT Pub. No.: WO2008/023373
PCT Pub. Date: Feb. 28, 2008

(65) Prior Publication Data
US 2010/0327262 A1    Dec. 30, 2010

Related U.S. Application Data

(63) Continuation-in-part of application No. 11/507,628, filed on Aug. 22, 2006, now Pat. No. 7,524,929, which is a continuation-in-part of application No. PCT/IL2006/000241, filed on Feb. 22, 2006.

(60) Provisional application No. 60/654,502, filed on Feb. 22, 2005, provisional application No. 60/847,614, filed on Sep. 28, 2006.

(51) Int. Cl.
*H01L 35/24* (2006.01)
(52) U.S. Cl.
USPC ..................................... 257/40; 257/E51.001
(58) Field of Classification Search
USPC ............................................. 257/40, E51.001
See application file for complete search history.

(56) References Cited

U.S. PATENT DOCUMENTS

| 6,231,983 B1 | 5/2001 | Lee et al. |
| 6,558,448 B2 | 5/2003 | Hu |
| 7,524,929 B2 | 4/2009 | Carmeli et al. |

(Continued)

FOREIGN PATENT DOCUMENTS

| DE | 19951616 | 5/2001 |
| JP | 04-009400 | 1/1992 |

(Continued)

OTHER PUBLICATIONS

Response Dated Jan. 25, 2011 to Office Action of Oct. 8, 2010 From the State Intellectual Property Office of the People's Republic of China Re. Application No. 200780038661.1.
Translation of Office Action Dated Oct. 8, 2010 From the State Intellectual Property Office of the People's Republic of China Re. Application No. 200780038661.1.
Official Action Dated Sep. 11, 2007 From the US Patent and Trademark Office Re.: U.S. Appl. No. 11/507,628.
Official Action Dated May 14, 2008 From the US Patent and Trademark Office Re.: U.S. Appl. No. 11/507,628.
Communication Pursuant to Article 94(3) EPC Dated Oct. 7, 2009 From the European Patent Office Re.: Application No. 06711223.5.
Communication Pursuant to Article 94(3) EPC Dated Nov. 12, 2008 From the European Patent Office Re.: Application No. 06711223.5.

(Continued)

*Primary Examiner* — Anthony Ho

(57) ABSTRACT

An optoelectronic device is disclosed. The device comprises one or more modified photocatalytic units, and a semiconductor surface. The modified photocatalytic unit is attached to the semiconductor surface such that when light is absorbed by the photocatalytic unit, an electric field is generated at sufficient amount to induce charge carrier locomotion within the semiconductor. In some embodiments a plurality of photocatalytic unit is attached to the semiconductor surface in oriented manner. The optoelectronic device can be operative in dry environment.

21 Claims, 12 Drawing Sheets
(9 of 12 Drawing Sheet(s) Filed in Color)

(56) References Cited

U.S. PATENT DOCUMENTS

| | | |
|---|---|---|
| 7,592,539 B2 | 9/2009 | Peumans et al. |
| 2003/0100127 A1 | 5/2003 | Corn et al. |
| 2003/0141498 A1 | 7/2003 | Stasiak |
| 2005/0098726 A1 | 5/2005 | Peumans et al. |

FOREIGN PATENT DOCUMENTS

| | | |
|---|---|---|
| WO | WO 96/18645 | 6/1996 |
| WO | WO 2004/013915 | 2/2004 |
| WO | WO 2006/060017 | 6/2006 |
| WO | WO 2006/090381 | 8/2006 |
| WO | WO 2008/018982 | 2/2008 |
| WO | WO 2008/023372 | 2/2008 |
| WO | WO 2008/023373 | 2/2008 |

OTHER PUBLICATIONS

International Preliminary Report on Patentability Dated Mar. 5, 2009 From the International Bureau of WIPO Re.: Application No. PCT/IL2007/001045.

International Preliminary Report on Patentability Dated Mar. 5, 2009 From the International Bureau of WIPO Re.: Application No. PCT/IL2007/001046.

International Preliminary Report on Patentability Dated Sep. 7, 2007 From the International Bureau of WIPO Re.: Application No. PCT/IL2006/000241.

International Search Report and the Written Opinion Dated May 9, 2008 From the International Searching Authority Re.: Application No. PCT/IL2007/001046.

International Search Report and the Written Opinion Dated Jun. 10, 2008 From the International Searching Authority Re.: Application No. PCT/IL2007/001045.

International Search Report and the Written Opinion Dated Jun. 29, 2006 From the International Searching Authority Re.: Application No. PCT/IL2006/000241.

Translation of Office Action Dated Sep. 25, 2009 From the State Intellectual Property Office of the People's Republic of China Re.: Application No. 200680013433.4.

Das et al. "Integration of Photosynthetic Protein Molecular Complexes in Solid-State Electronic Devices", Nano Letters, 4(6): 1079-1083, 2004.

Frolov et al. "Fabrication of A Photoelectronic Device by Direct Chemical Binding of the Photosynthetic Reaction Center Protein to Metal Surfaces", Advanced Materials, XP002384295, 17(20): 2434-2437, 2005.

Haick et al. "Effect of Molecular Binding to A Semiconductor on Metal/Molecule/Semiconductor Junction Behavior", Journal of Physical Chemistry B, ACS, XP002474764, 109(19): 9622-9630, May 19, 2005. p. 9622, col. 1, Lines 20-22, p. 9623, col. 1, Lines 24-26, 31-34, 50-53.

Lee et al. "Platinization: A Novel Technique to Anchor Photosystem I Reaction Centres Onto A Metal Surface at Biological Temperature and pH", Biosensors & Bioelectronics, 11(4): 375-387, 1996.

Meshulam et al. "Construction of Dithiol-Based Nanostructures by A Layer-Exchange Process", Small, XP002474763, 1(8-9): 848-851, Aug. 2005. p. 850, col. 2, Lines 5-22, Fig.4.

Millsaps et al. "Nanoscale Photosynthesis: Photocatalytic Production of Hydrogen by Platinized Photosystems I Reaction Centers", Photochemistry and Photobiology, 73(6): 630-635, 2001.

Nakamura et al. "Self-Assembling Photosynthetic Reaction Centers on Electrodes for Current Generation", Applied Biochemistry and Biotechnology, 84-86: 401-408, 2000.

Navarro et al. "Negatively Charged Residues in the H Loop of PsaB Subunit in the Photosystem I From Synechocystis Sp. PCC 6803 Appear to Be Responsible for Electrostatic Repulsions With Plastocyanin", Photosynthesis Research, 65: 63-68, 2000.

Radziemska "Thermal Performance of Si and GaAs Based Solar Cells and Modules: A Review", Progress in Energy and Combustion Science, 29: 407-424, 2003. Abstract.

Sarikaya et al. "Molecular Biomimetics: Nanotechnology Through Biology", Nature Materials, XP002478257, 2(9): 28-36, Feb. 2005. p. 578, col.3-p. 580, col. 2.

Sun et al. "Oxidizing Side of the Cyanobacterial Photosystem I. Evidence for Interaction Between the Electron Donor Proteins and A Luminal Surface Helix of the PsaB Subunit", The Journal of Biological Chemistry, 274(27): 19048-19054, 1999.

Sun et al. "Oxidizing Side of the Cyanobacterial Photosystem I: Mutational Analysis of the Luminal H Loop of the PsaB Subunit", Photosynthesis Research, 62: 241-250, 1999.

Sun et al. "Topography of the Photosystem I Core Proteins of the Cyanobacterium *Synechocystis* Sp. PCC 6803", The Journal of Biological Chemistry, 272(35): 21793-21802, 1997.

Trammell et al. "Orientated Binding of Photosynthetic Reaction Centers on Gold Using Ni-NTA Self-Assembled Monolayers", Biosensors and Bioelectronics, 19(12): 1649-1655, 2004.

Whaley et al. "Selection of Peptides With Semiconductor Binding Specificity for Directed Nanocrystal Assembly", Nature, XP002342143, 405: 665-668, Jun. 8, 2000. p. 665, col. 1, Lines 1-24, col. 2, Lines 5-6, p. 667, col. 2, Lines 51-53.

Yue et al. "Understanding Interfacial Electron Transfer to Monolayer Protein Assemblies", Current Opinion in Solid State and Materials Science, XP005482034, 9(1-2): 28-36, Feb. 2005. p. 2, 3.

Zeng et al. "Stabilization of Iron-Sulfur Cluster Fx by Intra-Subunit Interactions Unraveled by Suppressor and Second Site-Directed Mutations in PsaB of Photosystem I", Biochimica et Biophysica Acta, 1556(2-3): 254-264, 2002.

Examination Report Dated Aug. 9, 2010 From the Government of India, Patent Office Re. Application No. 4156/CHENP/2007.

Response Dated Feb. 9, 2011 to Examination Report of Aug. 9, 2010 From the Government of India, Patent Office Re. Application No. 4156/CHENP/2007.

Response Dated Dec. 20, 2010 to Office Action of Oct. 19, 2010 From the State Intellectual Property Office of the People's Republic of China Re.: Application No. 200680013433.4.

Translation of Office Action Dated Mar. 14, 2011 From the State Intellectual Property Office of the People's Republic of China Re. Application No. 200780038661.1.

Official Action Dated Apr. 4, 2011 From the US Patent and Trademark Office Re. U.S. Appl. No. 12/385,083.

Response Dated Jan. 18, 2010 to Office Action of Sep. 25, 2009 From the State Intellectual Property Office of the People's Republic of China Re.: Application No. 200680013433.4.

Response Dated Jan. 20, 2010 to Communication Pursuant to Article 93(4) EPC of Oct. 7, 2009 From the European Patent Office Re.: Application No. 06711223.5.

Sarikaya et al. "Molecular Biomimetics: Nanotechnology Through Biology", Nature Materials, XP002478257, 2(9): 28-36, Feb. 2005. p. 578, col. 3-p. 580, col. 2.

Communication Under Rule 71(3) EPC Dated May 17, 2011 From the European Patent Office Re.: Application No. 06711223.5.

Communication Pursuant to Article 94(3) EPC Dated May 6, 2010 From the European Patent Office Re.: Application No. 06711223.5.

Official Action Dated Jul. 18, 2011 From the US Patent and Trademark Office Re. U.S. Appl. No. 12/385,083.

Official Action Dated Nov. 15, 2011 From the US Patent and Trademark Office Re. U.S. Appl. No. 12/385,083.

Response Dated Aug. 31, 2010 to Communication Pursuant to Article 94(3) EPC of May 6, 2010 From the European Patent Office Re.: Application No. 06711223.5.

Translation of Office Action Dated Jun. 8, 2011 From the State Intellectual Property Office of the People's Republic of China Re. Application No. 200780038624.0.

Translation of Office Action Dated Oct. 19, 2010 From the State Intellectual Property Office of the People's Republic of China Re.: Application No. 200680013433.4.

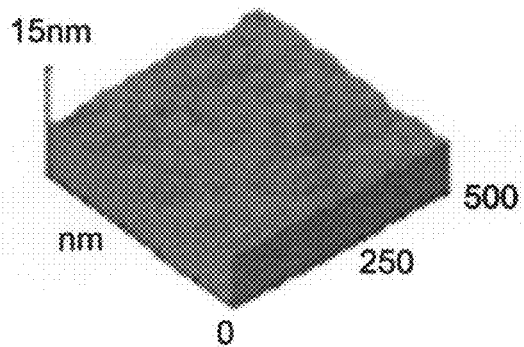
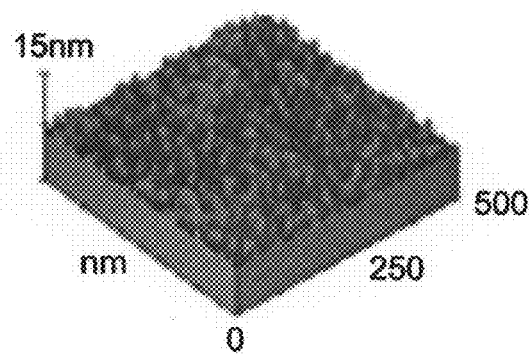
Fig. 2a        Fig. 2b
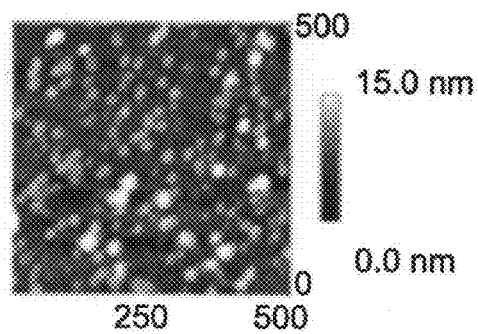
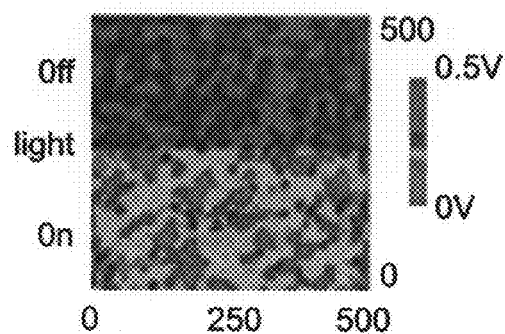
Fig. 2c        Fig. 2d
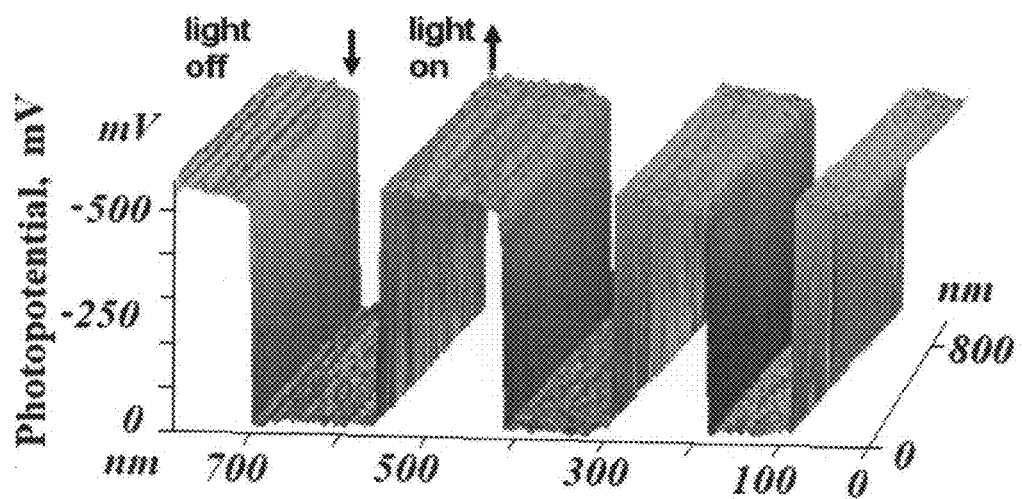
Fig. 2e

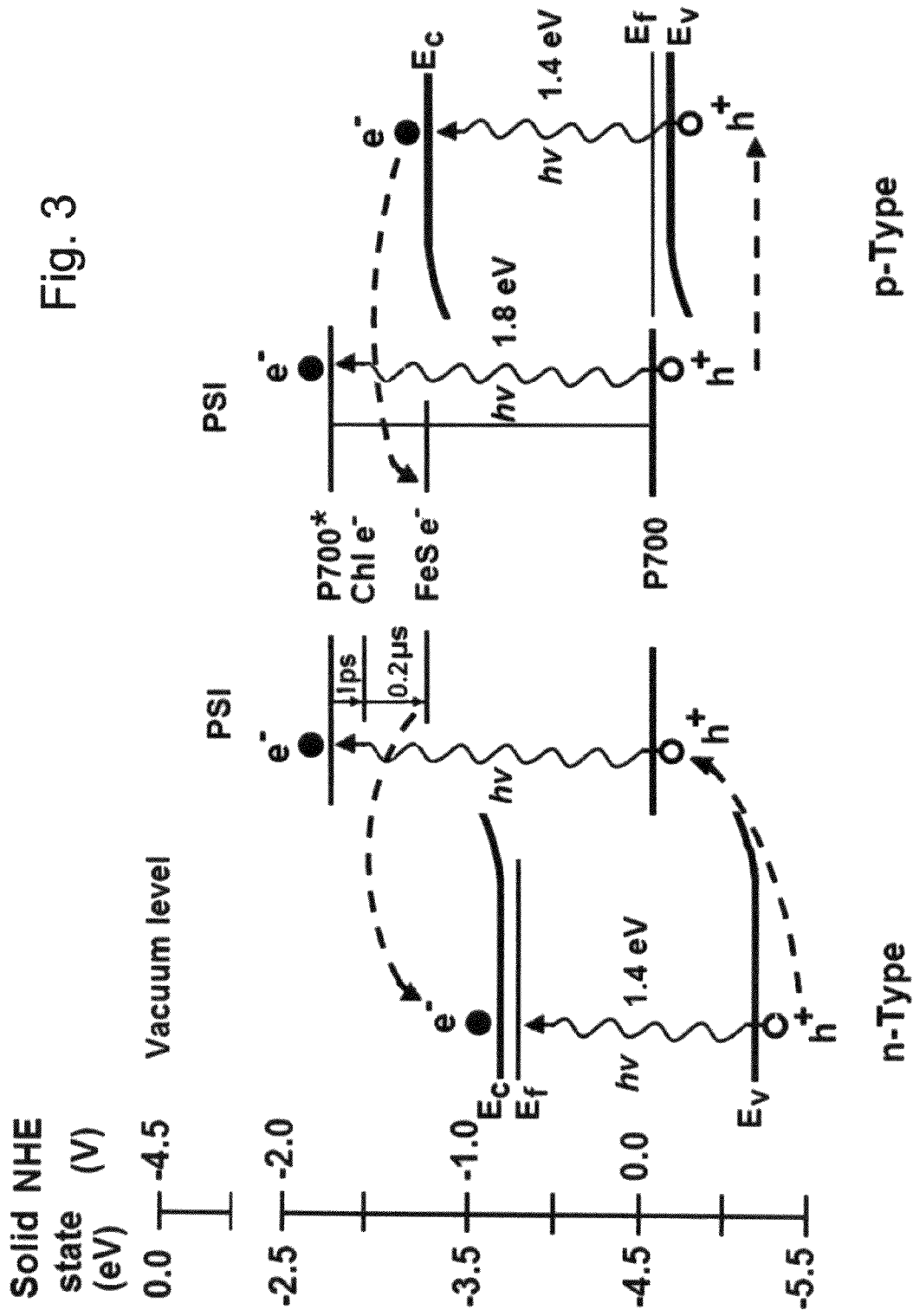

OPTOELECTRONIC DEVICE AND METHOD OF FABRICATING THE SAME

RELATED APPLICATIONS

This application is a National Phase Application of PCT Patent Application No. PCT/IL2007/001046 having International Filing Date of Aug. 22, 2007, which claims the benefit of U.S. Provisional Patent Application No. 60/847,614, filed on Sep. 28, 2006, and also is a Continuation-In-Part (CIP) of U.S. patent application Ser. No. 11/507,628, filed on Aug. 22, 2006, which is a Continuation-In-Part (CIP) of PCT Patent Application No. PCT/IL2006/000241, filed on Feb. 22, 2006, which claims the benefit of U.S. Provisional Patent Application No. 60/654,502, filed on Feb. 22, 2005. The contents of the above Applications are all incorporated herein by reference.

FIELD AND BACKGROUND OF THE INVENTION

The present invention relates to an optoelectronic device and, more particularly, to an optoelectronic device having photocatalytic units.

Green plants, cyanobacteria and photosynthetic bacteria capture and utilize sunlight by means of reaction centers embedded in their membranes. In oxygenic plants and cyanobacteria, photon capture and conversion of light energy into chemical energy take place in specialized membranes called thylakoids. The thylakoids are located in chloroplasts in higher plants or consists of foldings of the cytoplasmic membrane in cyanobacteria. The thylakoids, consisting of stacked membrane disks (called grana) and unstacked membrane disks (called stroma). The thylakoid membrane contains two key photosynthetic components, photosystem I and photosystem II, designated PS I and PS II, respectively. Photosynthesis requires PSII and PSI working in sequence, using water as the source of electrons and $CO_2$ as the terminal electron acceptor.

PS I is a transmembrane multisubunit protein-chlorophyll complex that mediates vectorial light-induced electron transfer from plastocyanin or cytochrome $C_{553}$ to ferredoxin. The nano-size dimension, the energy yield of approximately 58% and the quantum efficiency of almost 1 makes the reaction center a promising unit for applications in molecular nanoelectronics.

The crystalline structures of PS I in *Synechococus elongatus* and plant chloroplast have been resolved. In cyanobacteria, the complex consists of 12 polypeptides, some of which bind 96 light-harvesting chlorophyll and 22 carotenoid pigment molecules. The electron transport chain in PS I contains a special pair of chlorophyll (P700) that transfer electrons following photo excitation in 1 picoseconds (ps) to a monomeric chlorophyll a (Chl), through two intermediate phylloquinones (PQ) and three [4Fe-4S] iron sulfur centers (FeS), the final acceptors that are reduced in 0.2 □.

Attempts to attach plant PS I and bacterial reaction centers to metal surfaces are described in Lee, I., Stubna, A. & Greenbaum, E, "Measurement of electrostatic potentials above single photosynthetic reaction center," J. Phys. Chem., B 104, 2439-2443 (2000); Das, R. et al., "Integration of photosynthetic protein molecular complexes in solid-state electronic devices," Nano Letters 4, 1079-1083 (2004); Frolov, et al., "Fabrication of Photo-Electronic Device by Direct Chemical Binding of the Photosynthetic Reaction Center Protein to Metal Surfaces", Adv. Mater. 17, 2434-2437 (2005); U.S. Patent Application No. 60/654,502 and International Patent Application No. IL2006/000241.

SUMMARY OF THE INVENTION

The present inventors have succeeded in combining biological proteins, particularly photoactive photosynthetic proteins in solid-state electronics. The present inventors have discovered that such combination can serve as semiconductor modulators for many applications, include, without limitation, photo-gating, photo-sensing, nanoelectronics memory systems, communications and photon energy conversion.

According to one aspect of the present invention there is provided an optoelectronic device. The device comprises at least one modified photocatalytic unit, and a semiconductor surface, wherein the at least one modified photocatalytic unit is attached to the semiconductor surface such that when light is absorbed by the photocatalytic unit, an electric field is generated at sufficient amount to induce charge carrier locomotion within the semiconductor surface. In some embodiments of the present invention the optoelectronic device is operative in dry environment.

According to another aspect of the present invention there is provided a field effect transistor device. The device comprises a semiconductor source layer, a semiconductor drain layer, a semiconductor channel layer and at least one layer of modified photocatalytic units deposited on a surface of the semiconductor channel layer in a manner such that when light is absorbed by the at least one photocatalytic unit, an electric field is generated at sufficient amount to induce charge carrier locomotion between the source and the drain through the channel.

According to still further features in the described embodiments the modified photocatalytic unit(s) comprises at least one modified polypeptide having an amino acid sequence of a polypeptide of a photocatalytic unit of a photosynthetic organism.

According to still further features in the described embodiments the modified photocatalytic unit(s) is indirectly attached to the semiconductor surface.

According to still further features in the described embodiments the indirectly attachment is via a monolayer of linker molecules.

According to still further features in the described embodiments the monolayer of linker molecules is chemisorbed on the semiconductor surface.

According to still further features in the described embodiments the photosynthetic organism is a green plant.

According to still further features in the described embodiments the photosynthetic organism is a cyanobacteria.

According to still further features in the described embodiments the photocatalytic unit is PS-I.

According to still further features in the described embodiments the photocatalytic unit is a *Synechosystis* sp. PCC 6803 photocatalytic unit.

According to still further features in the described embodiments the amino acid sequence of the polypeptide of the photocatalytic unit comprises at least one substitution mutation.

According to still further features in the described embodiments the substitution mutation is on an extra-membrane loop of the photocatalytic unit.

According to still further features in the described embodiments the amino acid sequence of the polypeptide is psaB.

According to still further features in the described embodiments the amino acid sequence of the polypeptide is psaC.

According to still further features in the described embodiments the Psa B comprises a substitution mutation in at least one position demarked by the coordinates D235C/Y634C.

According to still further features in the described embodiments the Psa C comprises a substitution mutation in at least one position demarked by the coordinates W31C.

According to still further features in the described embodiments the at least one substitution mutation is cysteine.

According to still further features in the described embodiments the surface is made of a semiconductor of n-type.

According to still further features in the described embodiments the surface is made of a semiconductor of p-type.

According to still further features in the described embodiments the surface is made of a semiconductor of i-type.

According to still further features in the described embodiments the surface is transparent.

According to still further features in the described embodiments the surface comprises GaAs.

According to still further features in the described embodiments the surface comprises GaN.

According to still further features in the described embodiments the surface comprises AlGaN.

According to still further features in the described embodiments the surface comprises at least one material selected from the group consisting of Si, Ge, SiGe, AlGaAs, InGaAs, InGaP, AlInP and GaInAsP.

According to still further features in the described embodiments the isolated polypeptide is in a monomeric form or a trimeric form.

According to still further features in the described embodiments there is a plurality of modified photocatalytic units orientated at a substantially similar direction with respect to the surface.

According to still further features in the described embodiments the modified photocatalytic units are arranged layer-wise at a substantially similar direction with respect to the surface.

According to still further features in the described embodiments a distance between each of the plurality of photocatalytic units is between 15-25 nm.

According to still further features in the described embodiments the device serves as a component in a photodiode.

According to still further features in the described embodiments the device serves as a component in a phototransistor.

According to still further features in the described embodiments the device serves as a component in a logic gate.

According to still further features in the described embodiments the device serves as a photogate in a field effect transistor.

According to still further features in the described embodiments the device serves as a component in an optocoupler.

According to still further features in the described embodiments the device serves as a component in a photodetector.

According to still further features in the described embodiments the device serves as a component in an optical switch.

According to still further features in the described embodiments the device serves as a component in an image sensor.

According to an additional aspect of the present invention there is provided a method suitable for manufacturing an optoelectronic device. The method comprises attaching at least one modified photocatalytic unit to a surface of a semiconductor material, in a manner such that when light is absorbed by the photocatalytic unit, an electric field is generated at sufficient amount to induce charge carrier locomotion within the semiconductor material.

According to an additional aspect of the present invention there is provided a method of fabricating a field effect transistor. The method comprises depositing a first semiconductor layer characterized by a first dopant concentration on a second semiconductor layer characterized by a second dopant concentration being higher than the first dopant concentration. The method further comprises depositing a source ohmic contact layer and a drain ohmic contact layer on the second semiconductor layer, the source ohmic contact layer being laterally displaced from the drain ohmic contact layer over the second semiconductor layer. The method further comprises etching the second semiconductor layer between the source and the drain ohmic contact layers to form a recess in the second semiconductor layer and to partially expose the first semiconductor layer. The method further comprises attaching at least one layer of modified photocatalytic unit in the first semiconductor layer in the recess, thereby fabricating the field effect transistor.

According to further features in embodiments of the invention described below, the attachment is effected by indirect attachment via a linker molecule or a layer of linker molecules.

According to still further features in the described embodiments the linker molecule or layer of linker molecules is chemisorbed on the surface.

According to still further features in the described embodiments the modified photocatalytic unit or layer of modified photocatalytic units is covalently attached to the linker molecule(s).

According to still further features in the described preferred embodiments the linker molecule(s) comprises amino silan linked molecules with a maleimide moiety.

According to still further features in the described preferred embodiments the attachment comprises reacting the modified photocatalytic unit(s) with the linker molecule(s) under aqueous conditions, so as to covalently attach the modified photocatalytic unit(s) to the linker molecule(s).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the drawings:

FIG. 1a shows a light-induced charge transfer in the PS I-semiconductor system. Light illumination along black arrows causes light-induced charge transfer across the electron transport chain labeled by red (space fill, red) in PS I modeled in a polypeptide back-boned structure with cysteine mutants D235C/634C shown as space fill, yellow (arrows). FIG. 1b shows a schematic presentation of a PS I monolayer (space fill model) attached by the chemisorption of EMCA molecules to the GaAs surface. FIG. 1c is an enlarged schematic presentation of the EMCA molecule chemical bonds in a boundary layer between the cysteine (rods) in PS I and the GaAs substrate (shown in FIG. 1b in the yellow box). The images of the coordinates were modeled by Swiss PDB Viewer software in a PDB 1JB0 file.

FIGS. 2a-b are three-dimensional scanning probe microscopy images of the oriented PS I on GaAs substrate. FIG. 2a is a topographic 3D image of the non-coated GaAs substrate. FIG. 2b is a topographic 3D image of the GaAs substrate coated with PS I monolayer.

FIGS. 2c-d are 2D a topographic and a surface light-induced potential images of the same set of PS I monolayer on the GaAs substrate, respectively.

FIGS. 2e-f are graphs of spatial and temporal light-induced reversible photoresponses of the dense PS I monolayer on n-GaAs substrate, respectively. The spatial potential distribution in FIG. 2e is obtained by imposing a binary distribution of illumination onto the PS I monolayer. The kinetic traces 1 and 3 of light-induced surface potential changes in FIG. 2f correspond to the n- and p-GaAs substrate coated with PS I monolayer, respectively; the traces 2 and 4 to n- and p-substrates without coating. Illumination was provided by a He—Ne laser at 632.8 nm, 5 mW/cm$^2$. The potential sign obtained from the Kelvin probe force microscopy (KPFM) feedback circuit, is opposite to sign of the measured contact potential difference (CPD).

FIG. 3 is an energy level diagram for a PS I-GaAs system. The n- and p-type GaAs band energies were determined by measurements of CPD in comparison with a graphite standard and known data. The redox levels of electron carriers in PS I were determined according the potential measured against normal hydrogen electrode (NHE). Solid state energy levels and NHE redox levels are plotted on a vertical axis. The decrease in surface photovoltage (SPV), which is the difference in contact potential difference between the surface and a prob in the dark and the light, occurs due to both electron transfer from the PS I monolayer to n-type GaAs and hole transfer from n-type GaAs to the PS I monolayer. In the case of p-type GaAs, the increase in SPV results from a light-induced reduction of the FeS. The experimentally measured Fermi-level $E_f$, lower boundary of conduction band $E_c$, and upper boundary of valence band $E_v$ are for the n-type GaAs −3.8, −3.7, −5.2, and −3.06 eV, respectively. The equivalent values for the p-type are −4.63, −3.35, −4.73, and −3.52 eV respectively. The energy levels of primary electron donor (P700), the primary (Chl) and the final (FeS) electron acceptors in PS I are −4.58, −3.06, −3.52 eV, respectively.

DESCRIPTION OF EXEMPLARY EMBODIMENTS

Figure 1A:
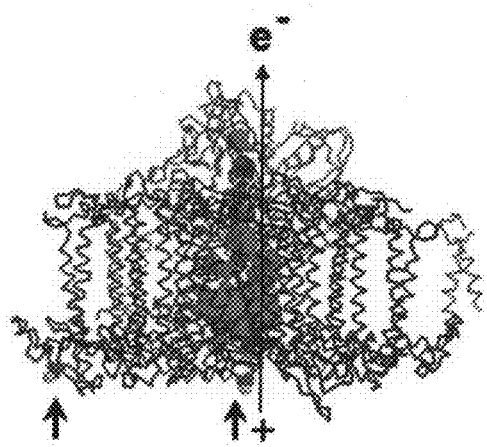
FIGS. 1a-c are schematic presentations of a molecular structure of PS I-GaAs system.
Figure 1B:
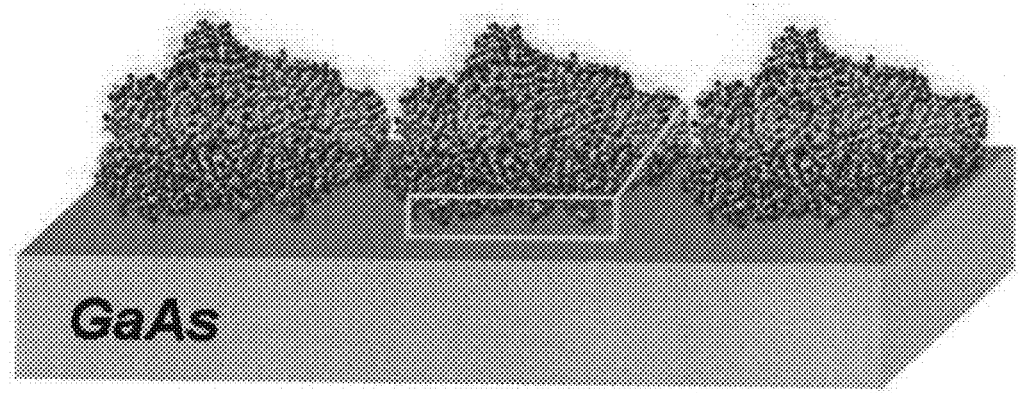

The present embodiments comprise a modified photocatalytic unit which can be covalently attached to a semiconductor substrate and maintain activity. Specifically, the present embodiments can be used as electronic components in a variety of optoelectronic devices.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Photosynthesis is the biological process that converts electromagnetic energy into chemical energy through light and dark reactions. In oxygenic plants and cyanobacteria, photon capture and conversion of light energy into chemical energy take place in specialized membranes called thylakoids. The thylakoids are located in chloroplast in higher plants or consists of foldings of the cytoplasmic membrane in cyanobacteria.

PS I is a transmembrane multisubunit protein-chlorophyll complex that mediates vectorial light-induced electron transfer from plastocyanin or cytochrome $C_{553}$ to ferredoxin. The nano-size dimension, an energy yield of approximately 58% and the high quantum efficiency make the reaction center into a promising unit for applications in molecular nano-electronics. However, in order to incorporate PS I reaction centers into molecular devices, it is essential to immobilize the PS I reaction centers onto a substrate without their denaturation. It is oftentimes desirable to immobilize the PS I reaction centers onto the substrate in oriented manner. An oriented attachment of the PS I reaction centers is advantageous so as to reduce or eliminate cancellation of induced electrical charges. It is oftentimes desirable to immobilize the PS I reaction centers onto the substrate such as to maintain the attachment and their catalytic activity in dry environment.

Polypeptides in photocatalytic units may be genetically modified, according to exemplary embodiments of the present invention such that they comprise functional groups for covalent binding to a semiconductor substrate whilst still retaining activity. As demonstrated in the Examples section that follows, amino acids in the Psa B polypeptide and Psa C polypeptide of the PS I in the extra membrane loops facing the cytoplasmic side of the bacterial membrane to cysteines were mutated to ensure formation of covalent bonds (between the PS I unit and a semiconductor substrate).

In various exemplary embodiments of the invention, photocatalytic unit are employed in an optoelectronic device.

As used herein, the phrase "photocatalytic unit" refers to a complex of at least one polypeptide and other small molecules (e.g. chlorophyll and pigment molecules), which when integrated together work as a functional unit converting light energy to chemical energy. As mentioned herein above, the photocatalytic units of the present invention are present in photosynthetic organisms (i.e. organisms that convert light energy into chemical energy). Examples of photosynthetic organisms include, but are not limited to green plants, cyanobacteria, red algae, purple and green bacteria.

Thus, examples of photocatalytic units which can be used in accordance with some embodiments of the present invention include biological photocatalytic units such as PS I and PS II, bacterial light-sensitive proteins, bacterial light-sensitive proteins, bacteriorhodopsin, photocatalytic microorganisms, pigments (e.g., proflavine and rhodopsin), organic dyes and algae. Preferably, the photocatalytic unit of the present invention is photosystem I (PS I).

PS I is a protein-chlorophyll complex, present in green plants and cyanobacteria, that is part of the photosynthetic machinery within the thylakoid membrane. It is ellipsoidal in shape and has dimensions of about 9 by 15 nanometers.

As used herein the term "about" refers to ±10%.

The PS I complex typically comprises chlorophyll molecules which serve as antennae which absorb photons and transfer the photon energy to P700, where this energy is captured and utilized to drive photochemical reactions. In addition to the P700 and the antenna chlorophylls, the PSI complex contains a number of electron acceptors. An electron released from P700 is transferred to a terminal acceptor at the reducing end of PSI through intermediate acceptors, and the electron is transported across the thylakoid membrane. Examples of PS I polypeptides are listed in Appendix 1 together with their source organisms.

According to a preferred embodiment of this aspect of the present invention, the PS I is derived from cyanobacteria and more specifically from *Synechosystis* sp. PCC 6803.

In cyanobacteria, the PS I complex consists of 12 polypeptides, some of which bind 96 light-harvesting chlorophyll and 22 beta carotenoid molecules. The electron transport chain contain P700, $A_0$, $A_1$, $F_X$, $F_A$ and $F_B$ representing a chlorophyll a dimmer, a monomeric chlorophyll a, two phylloquinones and three [4Fe-4S] iron sulfur centers, respectively. The reaction center core complex is made up of the heterodimeric PsaA and PsaB subunits, containing the primary electron donor, P700, which undergoes light-induced charge separation and transfers an electron through the sequential carriers $A_0$, $A_1$ and $F_X$. The final acceptors $F_A$ and $F_B$ are located on another subunit, PsaC.

PS Is derived from cyanobacteria are more structurally stable than those derived from plant and bacterial reaction centers. This is due to the fact that all chlorophyll molecules and carotenoids are integrated into the core subunit complexes in cyanobacteria while in plant and other bacterial reaction centers the antenna chlorophylls are bound to chlorophyll-protein complexes that are attached to the core subunits. Thus, unlike PS Is derived from other organisms such as plants and other bacteria, those derived from cyanobacteria do not require peptide surfactants for stabilization [R. Das et al., *Nano Letters* 2004, 4 1079-1083] during attachment to a solid surface under dry environment.

As used herein, the term "isolated" refers to the modified photocatalytic polypeptide that has been at least partially removed from its natural site of synthesis (e.g., photosynthetic organism). Typically, the photocatalytic polypeptide is not isolated from other members of the photocatalytic unit (i.e. chlorophyll and pigment) so that the photocatalytic unit remains functional. Preferably the polypeptide is substantially free from other substances (e.g., other cells, proteins, nucleic acids, etc.) that are present in its in-vivo location. The activity of the photocatalytic units of the present embodiments may be tested following the isolation.

As mentioned, the photocatalytic unit of this aspect of the present invention comprises the modified polypeptide.

The term "polypeptide" as used herein refers to a polypeptide which may be synthesized by recombinant DNA technology.

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

As used herein, the phrase "modified polypeptide" refers to a polypeptide comprising a modification as compared to the wild-type polypeptide. Typically, the modification is an amino acid modification. Any modification to the sequence is envisaged according to this aspect of the present invention so long as the polypeptide is capable of covalent attachment to a solid surface and retains a photocatalytic activity. Examples of modifications include a deletion, an insertion, a substitution and a biologically active polypeptide fragment thereof. Insertions or deletions are typically in the range of about 1 to 5 amino acids.

The site of modification is selected according to the suggested 3D structure of the photocatalytic unit. Evidence relating to the 3D structure of photocatalytic units may be derived from X-ray crystallography studies or using protein modeling software. The crystalline structure of PS I from *Synechococus elongatus* and from plants chloroplast has been resolved to 2.5 Å at 4.4 Å, respectively [P. Jordan, et al., *Nature* 2001, 411 909-917; A. Ben Shem, F. Frolow, N. Nelson, *Nature* 2003, 426 630-635].

The amino acid to be replaced or the site of insertion is typically on the external surface of the photocatalytic unit (e.g. on an extra membrane loop). Preferably, the amino acids to be replaced or the site of insertion is in a position which does not cause steric hindrance. Also it is preferred that the mutations are positioned near the P700 of the photocatalytic unit to secure close proximity between the reaction center and the solid surface in order to facilitate an efficient electric junction.

According to a preferred embodiment of this aspect of the present invention, the modification is a substitution (i.e. replacement) comprising a functional group side chain which is capable of mediating-binding to the solid surface. Particularly preferred coordinates for mutation of PS I from *Synechocystis* sp. PCC 6803 in PsaB include single mutations D235C, S246C, D479C, S499C, S599C and Y634C or double mutations D235C/Y634C and S246C/Y634C. In PsaC, a particularly preferred site for a mutation is W31C. In addition, a triple mutation may be generated in the photocatalytic units (e.g. PsaC//PsaB W31C//D235C/634C).

Preferably, the wild type amino acid which is substituted is not essential for the activity of the photocatalytic unit. Guidance in determining which amino acids are functionally redundant may be found by comparing the sequence of the photocatalytic unit with that of homologous known protein molecules and minimizing the number of amino acid sequence changes made in regions of high homology.

In one embodiment, conservative amino acid substitutions are made at one or more predicted, non-essential amino acid residues. A "conservative amino acid substitution" is one in which the amino acid residue is replaced with an amino acid residue having a similar side chain. Families of amino acid residues having similar side chains have been defined within the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In another embodiment, non-conservative amino acid substitutions may be made since the mutations are preferably designed to enable oriented covalent attachment of the protein to metal. By selecting mutant cells that can grow photoautotrophically, undamaged PS I cells may be ensured.

Preferably, the amino acids at the coordinates described hereinabove are replaced with an amino acid which is capable of binding to a metal surface—e.g. amino acids that comprise a thiol group such as cysteine.

Recombinant techniques are preferably used to generate the polypeptides of the present invention since photocatalytic units typically comprise more than one polypeptide and other molecules (e.g. pigment molecules and chlorophyll) integrated into a complex. In addition, these techniques are better suited for generation of relatively long polypeptides (e.g., longer than 20 amino acids) and large amounts thereof. Such recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

The polypeptides of the present invention may be modified by standard techniques, such as site-directed mutagenesis (oligonucleotide-mediated mutagenesis) and PCR-mediated mutagenesis. Thus a polynucleotide encoding a polypeptide of a photocatalytic unit may be mutated. Following mutagenesis the photocatalytic units can be expressed in an appropriate cell system.

Oligonucleotide-mediated mutagenesis is a technique which is well known in the art as described by Adelman et al., DNA, 2: 183 (1983). Briefly, a polynucleotide encoding a polypeptide of a photocatalytic unit (e.g. PsaB gene) is altered by hybridizing an oligonucleotide encoding the desired mutation to a polynucleotide template, where the template is the single-stranded form of the plasmid containing the unaltered or native polynucleotide sequence of the polypeptide of the photocatalytic unit. After hybridization, a DNA polymerase (e.g. Klenow fragment of DNA polymerase I) is used to synthesize an entire second complementary strand of the template that will thus incorporate the oligonucleotide primer, and will code for the selected alteration in the photocatalytic unit polynucleotide, thus producing a heteroduplex molecule.

This heteroduplex molecule is then transformed into a suitable host cell, usually a prokaryote such as *E. coli* JM101. After the cells are grown, they may be plated onto agarose plates and screened identify the bacterial colonies that contain the mutated DNA. The mutated region is then removed and placed in an appropriate vector for protein production, generally an expression vector of the type typically employed for transformation of an appropriate host.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded polynucleotide template molecule. The oligonucleotides are readily synthesized using techniques known in the art such as that described by Crea et al., Proc. Natl. Acad. Sci. USA, 75: 5765 (1978).

The polynucleotide template can only be generated by those vectors that are either derived from bacteriophage M13 vectors (the commercially available M13 mp18 and M13 mp19 vectors are suitable), or those vectors that contain a single-stranded phage origin of replication as described by Viera et al. Meth. Enzymol., 153: 3 (1987). Thus, the polynucleotide that is to be mutated must be inserted into one of these vectors to generate single-stranded template. Production of the single-stranded template is described in Sections 4.21-4.41 of Sambrook et al., Molecular Cloning: A Laboratory Manual (Cold Spring Harbor Laboratory Press, N.Y. 1989)

Mutants with more than one amino acid to be substituted may also be generated, using site directed mutagenesis.

PCR mutagenesis and cassette mutagenesis are also techniques that are suitable for modifying polypeptides of photocatalytic units—See Sambrook and Russell (2001, Molecular Cloning, A Laboratory Approach, Cold Spring Harbor Press, Cold Spring Harbor, N.Y.) and Ausubel et al. (2002, Current Protocols in Molecular Biology, John Wiley & Sons, NY).

Suitable hosts for the expression of the mutated photocatalytic sequences include any host that is capable of synthesizing a functional photocatalytic unit. Thus the host must be capable of incorporating pigment, chlorophyll molecules and the like into the unit. Examples of suitable hosts include, but are not limited to green plant cell cultures, green plants and photosynthetic bacteria. In a preferred embodiment of this aspect of the present invention, the host is *Synechocystis* bacteria.

According to a particularly preferred embodiment of the present invention, the mutated DNA is cloned by insertion into the host genome. This is particularly suitable when the host cell are photosynthetic bacteria. This method is affected by including in the vector a DNA sequence that is complementary to a sequence found in the photosynthetic genomic DNA. Transfection of photosynthetic bacteria with this vector results in homologous recombination with the genome and insertion of the photocatalytic poypeptide DNA.

The phrase "an isolated polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

As mentioned hereinabove, polynucleotide sequences of the present invention may be inserted into expression vectors (i.e., a nucleic acid construct) to enable expression of the recombinant polypeptide. The expression vector of the present invention includes additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals).

In bacterial systems, a number of expression vectors can be advantageously selected depending upon the use intended for the polypeptide expressed. For example, when large quantities of polypeptides are desired, vectors that direct the expression of high levels of the protein product, possibly as a fusion with a hydrophobic signal sequence, which directs the expressed product into the periplasm of the bacteria or the culture medium where the protein product is readily purified may be desired. Certain fusion protein engineered with a specific cleavage site to aid in recovery of the polypeptide may also be desirable. Such vectors adaptable to such manipulation include, but are not limited to, the pET series of E. coli expression vectors [Studier et al., Methods in Enzymol. 185:60-89 (1990)].

In cases where plant expression vectors are used, the expression of the polypeptide coding sequence can be driven by a number of promoters. For example, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] can be used. Alternatively, plant promoters can be used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)].

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

Expression and cloning vectors should contain a selection gene, also termed a selectable marker. This is a gene that encodes a protein necessary for the survival or growth of a host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, e.g. ampicillin, neomycin, methotrexate, or tetracycline, (b) complement auxotrophic deficiencies, or (c) supply critical nutrients not available from complex media.

Various methods can be used to introduce the expression vector of the present invention into the host cell system. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Transformed cells are cultured under effective conditions, which allow for the expression of high amounts of recombinant polypeptide. Effective culture conditions include, but are not limited to, effective media, bioreactor, temperature, pH and oxygen conditions that permit protein production. An effective medium refers to any medium in which a cell is cultured to produce the recombinant polypeptide of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes and petri plates. Culturing can be carried out at a temperature, pH and oxygen content appropriate for a recombinant cell. Such culturing conditions are within the expertise of one of ordinary skill in the art.

Following culturing under suitable conditions, the photocatalytic units are preferably isolated from the cells. An exemplary method for removing photocatalytic units from photosynthetic organisms is described in Example 2 of the Examples section hereinbelow. The present invention also envisages using any other methods of purification and isolation so long as the photocatalytic unit remains functional. The photocatalytic units may be isolated as polymers e.g. trimers or as single monomers. The photocatalytic units may be fully isolated or part of a membrane preparation. Methods of preparing membrane extracts are well known in the art. For example, Qoronfleh et al., [J Biomed Biotechnol. 2003; 2003 (4): 249-255] teach a method for selective enrichment of membrane proteins by partition phase separation. Various kits are also commercially available for the preparation of membrane extracts such as from Sigma-Aldrich (ProteoPrep™ Membrane Extraction Kit).

Preferably, one or more amino acid sequences of a polypeptide of the photocatalytic unit is attached to a semiconductor surface such as to allow charge carrier transfer between the amino acid sequence(s) and the semiconductor surface. The semiconductor surface can comprise GaAs, Si, Ge, GeN, SiGe, AlGaAs, InGaAs, InGaP, AlInP, GaInAsP, GaN, AlGaN, and the like.

GaAs absorbs in the same wavelength region with PS I. This can lead to photon absorption by the underlying GaAs. When it is desired to prevent photon absorption by the semiconductor, the photocatalytic unit and the semiconductor material are preferably selected to have different absorption spectra. For example, a modified PS I can be covalently attached to GaN or AlGaN.

Figure 12:
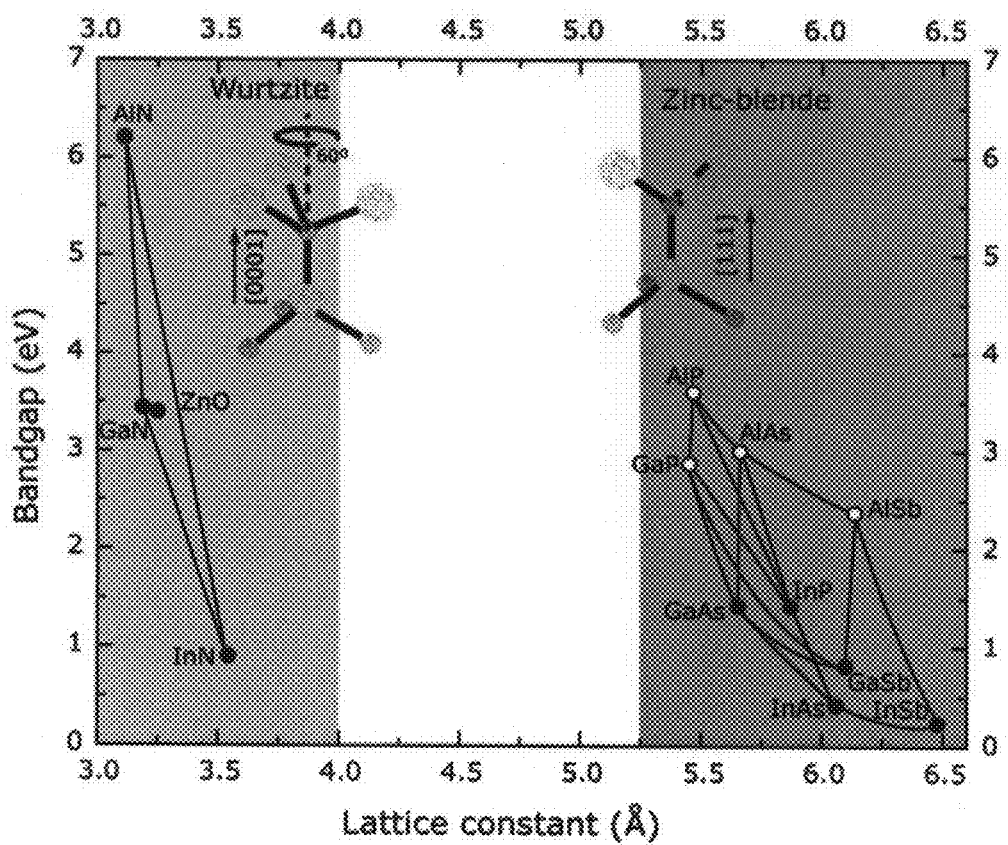
FIG. 12 shows the bandgap as a function of the lattice constant.

FIG. 12 shows the bandgap as a function of the lattice constant of III-V nitride semiconductors and other III-V semiconductors including GaAs. For AlN, GaN and InGaN a high two dimensional carrier concentration (above 3E13 $cm^{-2}$) can be achieved a few nanometers below the surface. This enables higher sensitivity to charge redistribution at the surface. AlN, GaN and InGaN are also compatible with biological systems. Additionally, blue and UV light emitting diodes can be fabricated on the same chip, permitting integrated source-detection sensing systems.

The polypeptide can be modified to facilitate its attachment (e.g., covalent attachment) to the semiconductor surface.

Attachment of the modified photocatalytic unit to the semiconductor surface can be effected indirectly using a linker molecule. For example, linker molecule can be chemisorbed on the semiconductor surface and the modified photocatalytic unit can be covalently attached to the chemisorbed molecule. When it is desired to attach a plurality of modified photocatalytic unit, the linked molecules can form a monolayer on the semiconductor surface. A representative example for such linked molecules is amino silan linked molecules with a maleimide moiety. This is particularly useful in the embodiments is which the substituting residue is cysteine, because the maleimide can readily attach to the cysteines in the modified photocatalytic unit. It was found by the present inventor that even though the linker molecules are short when compared with the size of the protein, their maleimide moiety can readily react with the cysteines to form a dense monolayer of photocatalytic units under aqueous conditions. It was further found by the present inventors that the short linker molecules ensure close packing of the units on the semiconductor surface. Such monolayer can includes particles of nanometric size. For example, the particles can have a diameter of about 15 nm and 20 nm, which respectively correspond to the size of monomers and trimers of PS I.

The semiconductor surface can be prepared for the attachment of the modified photocatalytic unit using the following procedure which is not intended to be limiting. The semiconductor surface can be cleaned and etched. Following rinsing, the etched semiconductor surface can be immediately immersed in a solution selected to facilitate chemical adsorption. For example, the solution can comprise ECMA, BMPA or the like which can be chemisorbed to the etched surface through their carboxyl end to form a self-assembled monolayer on the surface. An aqueous solution can be used for terminating the chemisoption.

The surface can be hydroxylated and then coated with amino silan using a reagent such as, but not limited to, (3-aminopropyl)-Diethoxymethylsilane or (3-aminopropyl) ethoxydimethylsilane. Linker molecules, e.g., m-Maleimidobenzoyl-N-hydroxysulfosuccinimide ester can then be attached to the amino silan.

According to some embodiments of the present invention, the modified photocatalytic unit retains photocatalytic activity following attachment to a solid surface.

Herein, the phrase "photocatalytic activity" refers to the conversion of light energy to chemical energy. Preferably, the modified photocatalytic units retain at least 20%, more preferably at least 30%, more preferably at least 40%, more preferably at least 50%, more preferably at least 60%, more preferably at least 70%, more preferably at least 80%, more preferably at least 90%, e.g., about 100% the activity of the wild type photocatalytic unit in its in-vivo environment. The present invention also envisages that the photocatalytic unit of the present invention comprises an activity greater than that of wild type photocatalytic unit in its in-vivo environment.

In various exemplary embodiments of the invention the photocatalytic units are attached in an oriented manner so as to prevent them, at least partially, from neutralizing each others charge.

Without being bound to any theory, the present inventors hypothesized that by substituting an identical amino acid for cysteine in a plurality of photocatalytic units, the attachment to a semiconductor surface can be oriented and the photocatalytic units form an oriented monolayer on the surface. The orientation of the photocatalytic units on the surface can be adjusted according to various exemplary embodiments of the present invention by judicious selection of the amino acid to be substituted by the cysteine residue.

Also contemplated is an oriented monolayer of photocatalytic units with inverted polarity. Reversing of the polarity of a photo-gate can be used to turn an n channel off or to turn on a p channel. For example, when PS I is employed an inverted polarity can be achieved by binding the reducing end of the PS I to the semiconductor surface. In this embodiment, a modified PS I having unique cysteine on subunit PsaC located on its reducing end can be used. Mutation W31C in PsaC subunit can be induced in native *Synechosystis* cell using vector p61-2.4. The isolated PS I complexes from mutant W31C in subunit PsaC in PS I can be used for fabrication of inversely orientated monolayer by attachment of the cysteine to maleimide moiety of linker molecules attached as a monolayer on the semiconductor surface.

Figure 6:
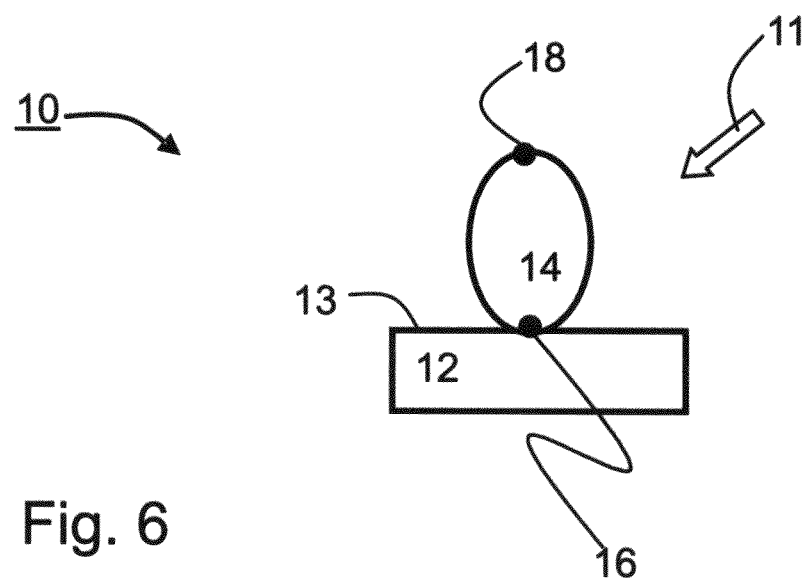
FIG. 6 is a schematic view of an optoelectronic device, according to various exemplary embodiments of the present invention.

FIG. 6 is a schematic illustration of an optoelectronic device 10, according to various exemplary embodiments of the present invention. Device 10 comprises a semiconductor substrate 12 and a plurality of isolated photocatalytic units 14 attached to a surface 13 of substrate 12. Isolated photocatalytic units 14 are preferably modified so as to facilitate covalent attachment of units 14 to surface 13, while maintaining the photocatalytic activity as further detailed hereinabove.

Being compose in part of photocatalytic units 14, optoelectronic device 10 facilitates light induced electron transfer. Upon excitation by light 11, an electron transfer occurs from a donor site 16, across multiple intermediate steps to an acceptor site 18, within a period of time which can be from several hundreds of picoseconds to a few microseconds, depending on the type of photocatalytic units. The frequency of light which induces the electron transfer depends on the photosynthetic organisms from which units 14 are obtained. For example, when photocatalytic units of green plants or green bacteria are employed, device 10 is sensitive to green light of wavelength of from about 400 nm to about 730 nm, when photocatalytic units of cyanobacteria are employed, device 10 is sensitive to light of wavelength of from about 400 nm to about 730 nm, when photocatalytic units of red algae are employed, device 10 is sensitive to red light of wavelength of from about 650 nm to about 700 nm and when photocatalytic units of purple bacteria are employed, device 10 is sensitive to purple light of wavelength of from about 400 nm to about 800 nm.

Optoelectronic device 10 can be used in the field of micro- and sub-microelectronic circuitry and devices including, but not limited to spatial imaging devices, solar batteries, optical computing and logic gates, optoelectronic switches, diodes, photonic A/D converters, and thin film "flexible" photovoltaic structures.

Figure 7:
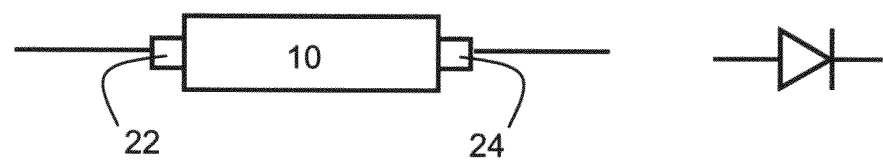
FIG. 7 is schematic view of a photodiode device, according to various exemplary embodiments of the present invention.

Reference is now made to FIG. 7, which is a schematic illustration of a photodiode device 20, according to various exemplary embodiments of the present invention. One skilled in the art will recognize that several components appearing in FIG. 6 have been omitted from FIG. 7 for clarity of presentation. Photodiode device 20 comprises optoelectric device 10, and two electrical contacts 22 and 24 being in electrical communication with donor site 16 and acceptor site 18, respectively. Electrical communication with donor site 16 can be established, for example, by connecting a conducting material to support 12 or surface 13. The acceptor site can be covalently bound by formation of sulfide bond between the modified polypeptide of the present invention (W31C in PsaC subunit of PS I) and the top deposited metal electrode. Platinized photocatalytic units at the acceptor side can make a metal to metal electrical connection with a top electrode deposited by evaporation of thin metal electrode. Deposition of conducting polymer on top of the photocatalytic monolayer or the platinized photocatalytic monolayer can serve as a top electrode. A symbolic illustration of the photodiode is illustrated on the right of FIG. 7.

In use, the photocatalytic units are irradiated by light hence being excited to efficient charge separation of high quantum efficiency, which is typically above 95%. Contacts 22 and 24 tap off the electrical current caused by the charge separation. Depending on the voltage applied between contacts 22 and 24, photodiode device 20 can be used either as a photovoltaic device, or as a reversed bias photodiode.

Specifically, in the absence of external voltage, photodiode device 20 enacts a photovoltaic device which produces current when irradiated by light. Such device can serve as a component in, e.g., a solar cell.

When reverse bias is applied between contacts 22 and 24, photodiode device 20 maintains high resistance to electric current flowing from contact 24 to contact 22 as long as photodiode device 20 is not irradiated by light which excites the photocatalytic units. Upon irradiation by light at the appropriate wavelength, the resistance is significantly reduced. Such device can serve as a component in, e.g., a light detector.

Optoelectronic device 10 can also serve as a solar cell, when no bias voltage is applied. Upon irradiation of the photocatalytic units, the charge-separated state results in internal voltage between donor site 16 and acceptor site 18. The internal voltage can be tapped off via electrical contacts at donor site 16 and acceptor site 18. If the current circuit is closed externally, the current flow is maintained through repeated light-driven charge separation in the solar cell.

The generated polarized charge-separated state of device 10 can also be utilized for in a molecular transistor. Specifically, device 10 can serve as a light-charged capacitor enacting a gate electrode which modifies the density of charge carriers in a channel connected thereto.

Figure 8:
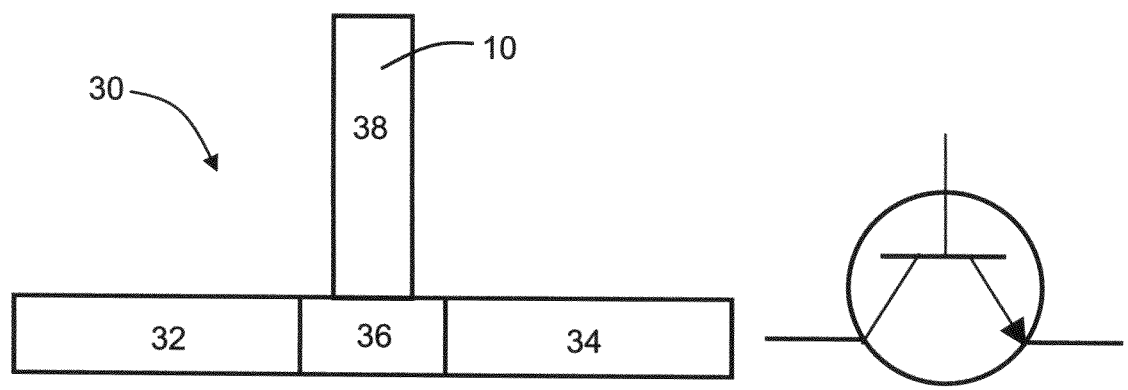
FIG. 8 is a schematic view of a phototransistor, according to various exemplary embodiments of the present invention.

Reference is now made to FIG. 8, which is a schematic illustration of a phototransistor 30, according to various exemplary embodiments of the present invention. Phototransistor 30 comprises a source electrode 32, a drain electrode 34, a channel 36 and a light responsive gate electrode 38. Gate electrode 38 preferably comprises optoelectronic device 10. Channel 36 preferably has semiconducting properties such that the density of charge carriers can be varied.

In the absence of light, channel 36 does not contain any free charge carriers and is essentially an insulator. Upon exposure to light, the photocatalytic units of device 10 generate a polarized charge-separated state and the electric field caused thereby attracts electrons (or more generally, charge carriers) from source electrode 32 and drain electrode 34, so that channel 36 becomes conducting. Thus, phototransistor 30 serves as an amplifier or a switching device where the light controls the current flowing from source electrode 32 and drain electrode 34.

The gate electrode can be formed from the isolated photocatalytic units of the present embodiments as further detailed hereinabove. A symbolic illustration of the phototransistor is illustrated at the right had side of FIG. 8.

As will be appreciated by one ordinarily skilled in the art, phototransistor 30 can operate while gate electrode 38 is left an open circuit because the gating is induced by photons impinging on electrode 38. Phototransistor 30 can be used as a logical element whereby the phototransistor can be switched to an "on" state by the incident light. In addition, phototransistor 30 can be used as the backbone of an image sensor with large patterning possible due to a strong variation of the drain current with the spatial position of the incident light beam. Several phototransistors, each operating at a different wavelength as further detailed hereinabove can be assembled to allow sensitivity of the image sensor to color images. The charge storage capability of the structure with further modifications known to one skilled in the art of conventional semiconductors can be exploited for memory related applications.

Photodiode 20 and/or phototransistor 30 can be integrated in many electronic circuitries. In particular, such devices can be used as building blocks which can be assembled on a surface structure to form a composite electronic assembly. For example, two or more photodiodes or phototransistors can be assembled on a surface structure to form a logic gate, a combination of logic gates or a microprocessor.

Figure 9:
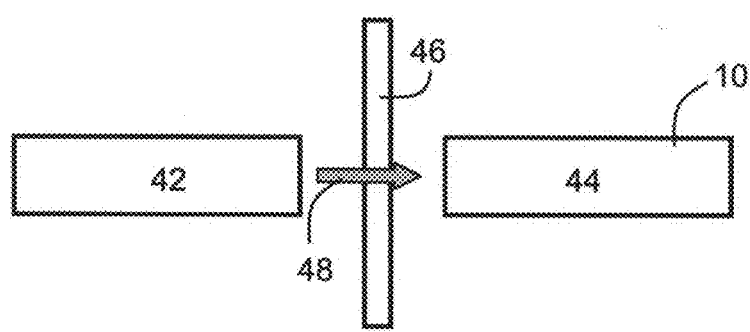
FIG. 9 is a simplified view of an optocoupler, according to various exemplary embodiments of the present invention.

Reference is now made to FIG. 9 which is a simplified illustration of an optocoupler 40, according to various exemplary embodiments of the present invention. Optocoupler 40 is particularly useful for transferring signals from one element to another without establishing a direct electrical contact between the elements, e.g., due to voltage level mismatch. For example, optocoupler 40 can be used to establish contact free communication between a microprocessor operating at low voltage level and a gated switching device operating at high voltage level.

According to a preferred embodiment of the present invention optocoupler 40 comprises an optical transmitter 42 and an optical receiver 44. Transmitter 42 can be any light source, such as, but not limited to, a light emitting diode (LED). Receiver 44 preferably comprises optoelectronic device 10, and can be, for example, a photodiode (e.g., photodiode 20) or a phototransistor (e.g., phototransistor 30). Transmitter 42 is selected such that the radiation emitted thereby is at sufficient energy to induce charge separation between donor site 16 and acceptor site 18 of device 10.

Transmitter 42 and receiver 44 are kept at optical communication but electrically decoupled. For example, transmitter 42 and receiver 44 can be separated by a transparent barrier 46 which allows the passage of light but prevents any electrical current flow thereacross. Transmitter 42 and receiver 44 preferably oppose each other such that the radiation emitted from transmitter 42 strikes receiver 44.

Triggered by an electrical signal, transmitter 42 emits light 48 which passes through barrier 46 and strikes receiver 44. In turn, receiver 44 generates an electrical signal which can be tapped off via suitable electrical contacts as further detailed hereinabove. Thus optocoupler 40 successfully transmits to its output (receiver 44) an electrical signal applied at its input (transmitter 42), devoid of any electrical contact between the input and the output.

Figures 10A, 10B:
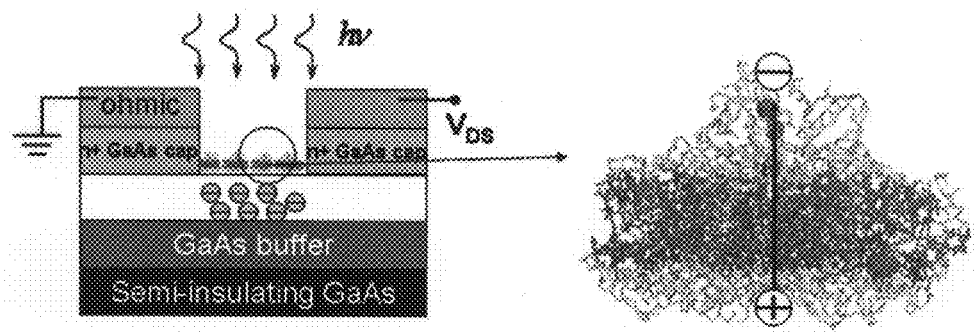
FIGS. 10a-c are schematic illustrations of a field effect transistor (FET), according to various exemplary embodiments of the present invention.
Figures 10C, 10D:
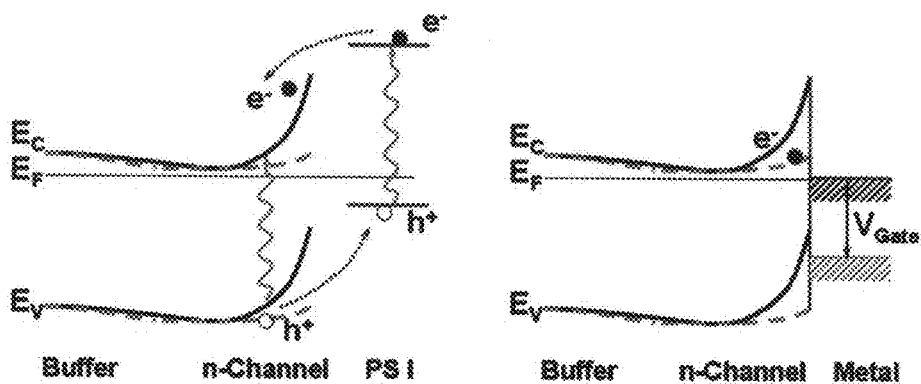
FIG. 10d is a band diagram of a traditional Schottky metal gated FET.

Reference is now made to FIGS. 10*a-c* which are schematic illustrations of a field effect transistor (FET), according to various exemplary embodiments of the present invention. Shown in FIG. 10*a* is a FET which comprises one or more layers of the modified photocatalytic units of the present embodiments. An enlarged modified photocatalytic unit is shown in FIG. 10*b*. FIG. 10*c* is a representative example of a band diagram, which, in the present example correspond to n-channel. For clarity of presentation, also provided is FIG. 10*d* which is a band diagram of a traditional Schottky metal gated FET.

Referring first to FIG. 10*d*, at zero gate bias (black lines), the semiconductor channel is partially depleted. When a more positive gate bias is applied (read lines), more charges are induced in the channel via capacitive coupling thus resulting in a larger current flowing between the source and drain.

The third terminal of the FET of the present embodiments is preferably modified photocatalytic unit, e.g., a modified PS I. Upon absorbing photons, electrons transfer into semiconductor thus increasing the conductivity of the channel; meanwhile, holes transfer to the modified photocatalytic unit attracting more electrons supplied from the ohmic contacts. Therefore, an open channel results (red lines in FIG. 10*c*). The induced photocurrent in the FET of the present embodiments is typically proportional to the ratio of the hole lifetime over the electron transit time from the source to the drain, and its switching characteristics depends on the two time constants.

Figure 13A:
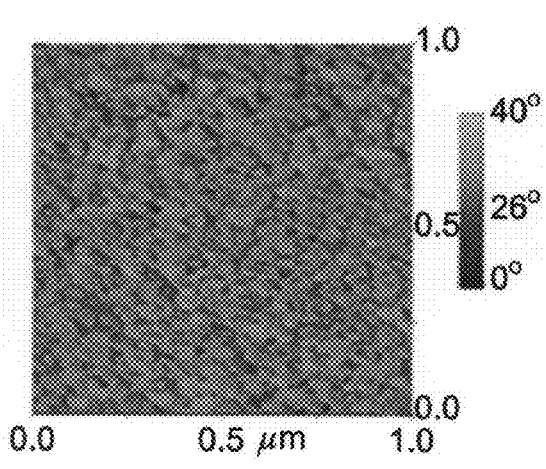
FIGS. 13a-b show phase contrast images of PS I (FIG. 13a) and platinized PS I (FIG. 13b), according to various exemplary embodiments of the present invention.
Figure 13B:
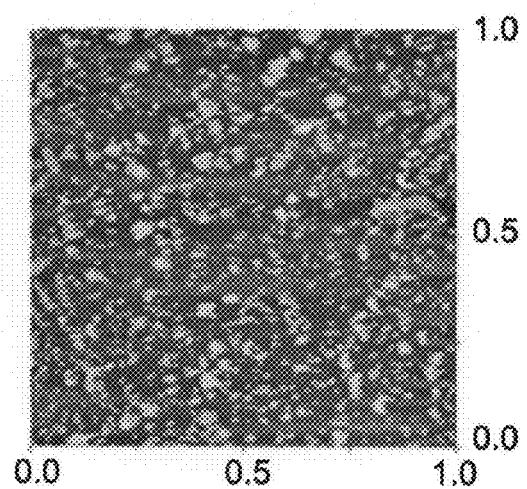

The absorption cross section, total quantum efficiency and the photopotential can be improved using more than one monolayer of photocatalytic units. This can be effected by a method which utilizes metal bonding by photoreducing $Pt^{4+}$ ions in solution by the PS I monolayer. $Pt^{4+}$ ions can be photoreduced by PS I monolayer at the reducing end of the protein and Pt is deposited. Such monolayer is characterized by metal deposition on top of each of the PS I as the phase angle increases with the stiffness of the substrate (see FIGS. 13*a* and 13*b* showing phase contrast images of PS I, and platinized PS I, respectively). Using such technique, several oriented monolayers can be formed on top of each other, where the Pt—S bond connects between adjacent monolayers.

The present embodiments successfully provide a method suitable for fabricating a field effect transistor. The method preferably begin by depositing a first semiconductor layer characterized by a first dopant concentration on a second semiconductor layer characterized by a second dopant concentration which is higher than the first dopant concentration. The two semiconductor layers can be either n-doped or p-doped layers. Optionally and preferably the first semiconductor layer is deposited on a semi-insolating semiconductor layer, such that the first layer is between the semi-insolating layer and the second layer.

The method can continue to a step in which a source ohmic contact layer and a drain ohmic contact layer are deposited on the second semiconductor layer. The source and drain ohmic contact layers are laterally displaced from each other over the second semiconductor layer. The method preferably continues by etching the second semiconductor layer between the source and the drain contact layers so as to form a recess in the second semiconductor layer. The etching is preferably done such as to partially expose the first semiconductor layer between the source and the drain.

Once the recess is formed, the method continues to a step in which one or more layers of modified photocatalytic unit are attached on a surface of the first semiconductor layer in the recess.

Figure 11A:
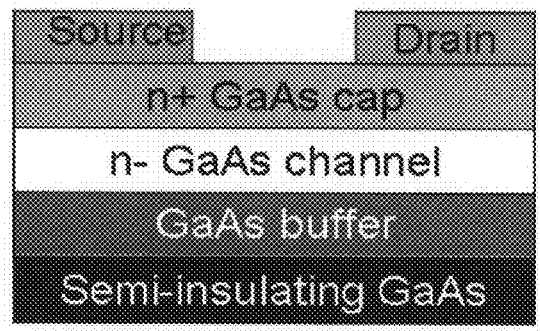
FIGS. 11a-c are schematic illustration of a process suitable for manufacturing a FET, according to various exemplary embodiments of the present invention.
Figure 11B:
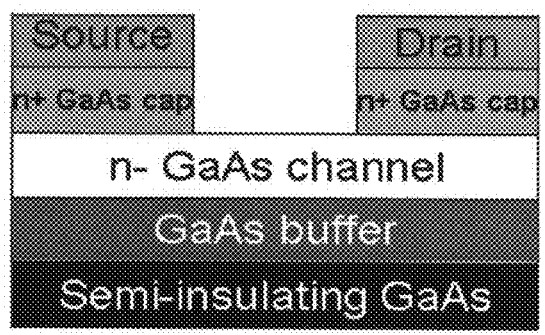
Figure 11C:
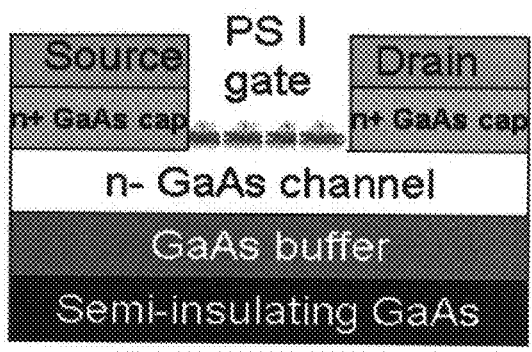

Reference is now made to FIGS. 11*a-c* which are schematic illustration of a process suitable for manufacturing a FET, according to various exemplary embodiments of the present invention.

While the embodiments below are described with a particular emphasis to a process in which the semiconductor is GaAs and the photocatalytic unit is PS I, it is to be understood that more detailed reference to such process is not to be interpreted as limiting the scope of the invention in any way. One of ordinary skills in the art, provided with the details described herein would know how to adjust the process of for any of the aforementioned semiconductor materials and any of the aforementioned types of photocatalytic units.

FIG. 11*a* illustrates a moderately doped GaAs channel with high carrier mobility is grown on top of GaAs buffer with very low background impurities on semi-insulating GaAs substrate, followed by a heavily doped GaAs cap layer. Ohmic contacts (such as, but not limited to, AuGe/Ni/Au for n-GaAs and ZnAu/Au for p-GaAs) are deposited on the top GaAs cap, e.g., using e-beam evaporation and alloyed. FIG. 11*b* illustrates self-aligned gate recess in the heavily doped GaAs region between the source and the drain, formed by etching using the ohmic contacts as etching mask. FIG. 11*c* illustrates formation of optically active gate by PS I functionalization, as described herein.

In various exemplary embodiments of the invention the sizes of the above electronic devices (including, without limitation, the optoelectronic device, solar cell, photodiode, phototransistor, logic gate, optocoupler and FET) are in the sub millimeter range. Preferably, the size of the electronic devices is from about 0.1 nm to about 100 □m, more preferably, from about 0.1 nm to about 1 □m.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Experimental Procedure

The robust PS I reaction center from the cyanobacteria *Synechosystis* sp. PCC 6803 was selected to ascertain whether genetic modifications could assist in attachment of the reaction center to a solid support. The main reason for the structural stability of the PS I is due to the fact that all chlorophyll molecules and carotenoids are integrated into the core subunits complex. Antenna chlorophylls in plant and bacterial reaction centers are bound to chlorophyll-protein complexes attached to the core subunits.

Selection of the amino acids to be modified to cysteines for covalent attachment of the PS I to the GaAs substrate was based on the knowledge of the atomic structure of the PS I.

Thus, amino acids in the extra membrane loops facing the cytoplasmic side of the bacterial membrane which do not have stereo hindrance when placed on a solid surface were mutated to cysteines in order to ensure formation of sulfide bonds.

The samples used in the present examples study were undoped, n (Zn)- and p (Si)-doped GaAs (Wafer Technology LTD) with a doping concentration of $1 \times 10^{18}$ cm$^{-3}$. The properties of GaAs indicate Hall mobility of 54743, 65 and 2305 cm$^2$V$^{-1}$s$^{-1}$ and resistivity of 9E8, 1E-2 and 3E-3 Ohm for the undoped, n- and p-doped, respectively. The samples were cleaned for 10 minutes in boiling acetone and then methanol successively, etched for 20 s in 5% HF, rinsed for 8 seconds first in deionized water and then in ethanol.

For chemical adsorption, the etched GaAs was immediately immersed for 8 h in an ethanol solution of 5 mM N-☐-maleimidocaproic acid (ECMA) or N-☐-maleimidopropionic acid (BMPA) (Pierce Biotechnology Inc) at 20° C. Chemisoption was terminated by rinsing in aqueous solution containing 20 mM Tris, pH 7, and 0.05% ☐-D-maltoside.

PS I molecules were indirectly attached to the surface by the formation of a covalent bond between the unique cysteine thiols in PS I mutants D235C/Y634C in PsaB subunits. The maleimide moiety in the linker molecules was chemisorbed to the GaAs surface. After rinsing the samples were immediately transferred to a solution containing the same buffer and 0.5 mg/ml chlorophyll of PS I for 2 h at 20° C. After incubation, the sample was washed in deionized water and dried in ultrapure nitrogen.

Site-directed mutagenesis was carried out in the psaB gene using the homologous recombination vector, pZBL-D235C/Y634C. Mutations were inserted by an overlapping extension PCR. PsaB-deficient recipient cells were transformed and the transformants were grown under autotrophic growth conditions as described in U.S. Patent Application No. 60/654,502 and Ser. No. 11/507,628, and in International Patent Application No. IL2006/000241.

AFM and KPFM measurements were conducted using both Nanoscope® IIIa MultiMode™ with Extender™ Electronics Module (Veeco Inc.) and Solver PH47, (NTMDT Inc.). Kelvin mode is based on the two-pass technique. In the first pass the topography is acquired using standard semicontact mode (mechanical excitation of the cantilever). In the second pass this topography is retraced at a set lift height from the sample surface to detect the electric surface potential. The operating frequency was around 300 kHz. CPD is extracted in the conventional way by nullifying the output signal of a lock-in amplifier which measures the electrostatic force at the first resonance frequency. The NTMDT AFM was equipped with a custom-made 1300-nm wavelength feedback laser to prevent any sample-induced photovoltage. Most CPD measurements were conducted in a nitrogen glove box. A comparison with an in-situ peeled pyrolitic graphite standard (OPG) enabled to extract the actual work function of all measured samples. A He—Ne laser ($\lambda=632.8$ nm, 5 mW/cm$^2$) was used for the photovoltage measurements.

Example 1

Detection of Photoresponse of PS I-n-GaAs System

Zn-doped GaAs substrates were cleaned for 10 minutes in boiling acetone and then methanol successively, etched for 20 s in 5% HF, rinsed for 8 seconds first in deionized water and then in ethanol. Further the etched GaAs substrates were immediately immersed for 8 h in an ethanol solution of 5 mM N-☐-maleimidocaproic acid (ECMA) or N-☐-maleimidopropionic acid (BMPA) (Pierce Biotechnology Inc) at 20° C. The chemisoption was terminated by rinsing in aqueous solution containing 20 mM Tris, pH 7, and 0.05% ☐-D-maltoside. The chemisorpted GaAs substrates were immediately transferred to a solution containing the same buffer and 0.5 mg/ml chlorophyll of PS I for 2 h at 20° C. After incubation, the samples were washed with deionized water and dried with ultrapure nitrogen.

The CPD values for the non-coated chemisorbed and PS I-coated n-GaAs substrates are specified in Table 1. Each value in Table 1 was averaged over 6 scanned (512×512 line) similar samples. $U_D$ and $U_L$ are CPD corresponding to illuminated and non-illuminated samples.

TABLE 1

| | Contact potential difference (V) | | |
|---|---|---|---|
| Sample | $U_D$ | $U_L$ | $U_L - U_D$ |
| n-GaAS | −0.405 ± 0.001 | −0.085 ± 0.001 | 0.32 ± 0.001 |
| n-GaAS-EMCA | −0.305 ± 0.001 | −0.053 ± 0.001 | 0.252 ± 0.001 |
| n-GaAS-EMCA-PSI | −0.359 ± 0.003 | −0.472 ± 0.001 | −0.113 ± 0.003 |
| n-GaAS-BMPA-PSI | −0.315 ± 0.003 | −0.451 ± 0.001 | −0.136 ± 0.003 |

Example 2

Detection of Photoresponse of PS I-p-GaAs System

Si-doped GaAs substrates were processed similar to Example 1. The CPD values for the non-coated chemisorbed, and PS I-coated p-GaAs substrates are specified in Table 2.

TABLE 2

| | Contact potential difference (V) | | |
|---|---|---|---|
| Sample | $U_D$ | $U_L$ | $U_L - U_D$ |
| p-GaAS | 0.350 ± 0.001 | 0.042 ± 0.001 | −0.308 ± 0.001 |
| p-GaAS-EMCA | 0.520 ± 0.005 | 0.040 ± 0.001 | −0.480 ± 0.005 |
| p-GaAS-EMCA-PSI | −0.152 ± 0.007 | 0.295 ± 0.001 | 0.447 ± 0.007 |
| p-GaAS-BMPA-PSI | −0.170 ± 0.003 | 0.248 ± 0.001 | 0.418 ± 0.003 |

Example 3

Detection of Photoresponse of PS I-u-GaAs System

Undoped GaAs substrates were processed similar to Example 1. The CPD values for the non-coated chemisorbed, and PS I-coated u-GaAs substrates are specified in Table 3.

TABLE 3

| | Contact potential difference (V) | | |
|---|---|---|---|
| Sample | $U_D$ | $U_L$ | $U_L - U_D$ |
| u-GaAS | −0.023 ± 0.003 | 0.062 ± 0.001 | 0.085 ± 0.003 |
| u-GaAS-EMCA | 0.160 ± 0.005 | 0.038 ± 0.001 | 0.022 ± 0.005 |
| u-GaAS-EMCA-PSI | −0.144 ± 0.001 | 0.265 ± 0.001 | 0.409 ± 0.001 |
| u-GaAS-BMPA-PSI | −0.185 ± 0.008 | 0.254 ± 0.001 | 0.439 ± 0.008 |

As shown in Tables 1-3, the etching and chemisorption of the EMCA and BMPA monolayers on the GaAs surface caused a 0.1 to 0.17 V increase of the CPD. This effect is assumed to be due to the formation of Ga carboxylate and to the dipole formed by a pair of exposed oxygen atoms at the maleimide ring. Similar changes in the surface energetics of semiconductors are affected by the chemisorption of organic and inorganic molecules and peptides used to modulate photonic crystals band gap energies [Bastide, S. et al. Controlling the work function of GaAs by chemisorption of benzoic acid derivatives. J. Phys. Chem. B 101, 2678-2684 (1997)].

Figure 1C:
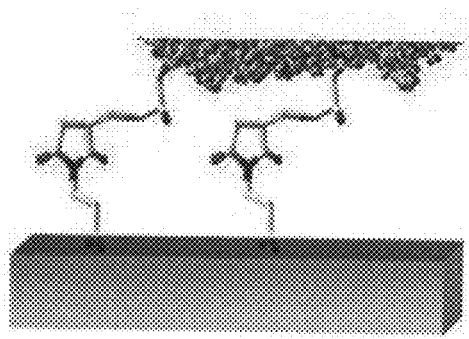

Decrease in the CPD (without illumination) caused by the bond formation between PS I and the GaAs (FIG. 1c) was 0.05 V, 0.31 V, and 0.67 V for the n-, u- and PS I-p-doped GaAs system, respectively. The difference in CPD between the n- and p-type GaAs can be explained by electron transfer from the PS I to the p-GaAs (see the energy levels diagram in FIG. 3). As shown in the diagram, the P700 ground state energy level is higher than the valence band maximum $E_v$ of both p- and n-GaAs. An electron, however, is transferred from the P700 level to the p-GaAs valence band but not to the n-GaAs because the latter valence band is fully occupied. Such an oxidation of PSI charges it positively and decreases the CPD in agreement with the experimental data of the present example. Similar results were obtained on the PS I-GaAs system chemisorbed with a monolayer of BMPA. Molecular structure of BMPA comprises one carbon atom less in comparison with EMCA molecular structure. These results demonstrate a direct electron transfer between large proteins, and, the GaAs substrate through the chemisorbed small molecule.

A very small photovoltage $U_L$ of −0.05, 0.06 and 0.04 V was measured in the EMCA-treated n-, u-, and p-GaAs, respectively. Such small changes are due mainly to the small band bending of the different GaAs surfaces. The chemisorption of the PS I monolayer, however, resulted in a much higher photovoltage $U_L$ of about 0.265 and 0.295 V for the u- and p-doped GaAs, respectively. Such a positive photovoltage $U_L$ is due to the light-induced charge separation and consequent electron transfer across the protein, resulting in a dipole formation. Negative charge of this dipole is at the reducing end of the PS I opposite to GaAs surface.

Surprisingly, the PS I monolayer bound to n-GaAs induced a negative photovoltage $U_L$ of −0.47 V. A change in the photovoltage polarity can be explained by comparing the energy of the GaAs bands with the redox potential energy levels of the primary donor and the electron acceptors in the PS I protein, illustrated together in FIG. 3. Difference between Fermi level $E_f$ and the conduction band minimum $E_c$ in p- and n-GaAs is about −0.8 and −0.235 eV, respectively. The energy level $E_c$ in n-GaAs is 0.5 and 0.24 eV lower relative to the primary (Chl) and the final (FeS) electron acceptor levels in PS I, respectively. Therefore, under illumination conditions, the electrons transfer from the PS I to the n-type GaAs, and the holes move from the semiconductor to the PS I; this effect charges positively the PS I, and decreases the surface potential.

Figure 2F:
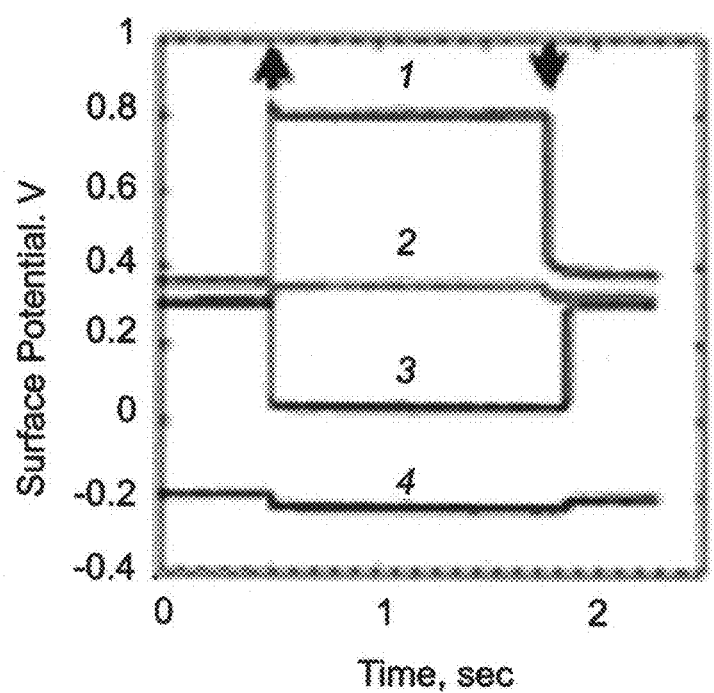
Figure 4:
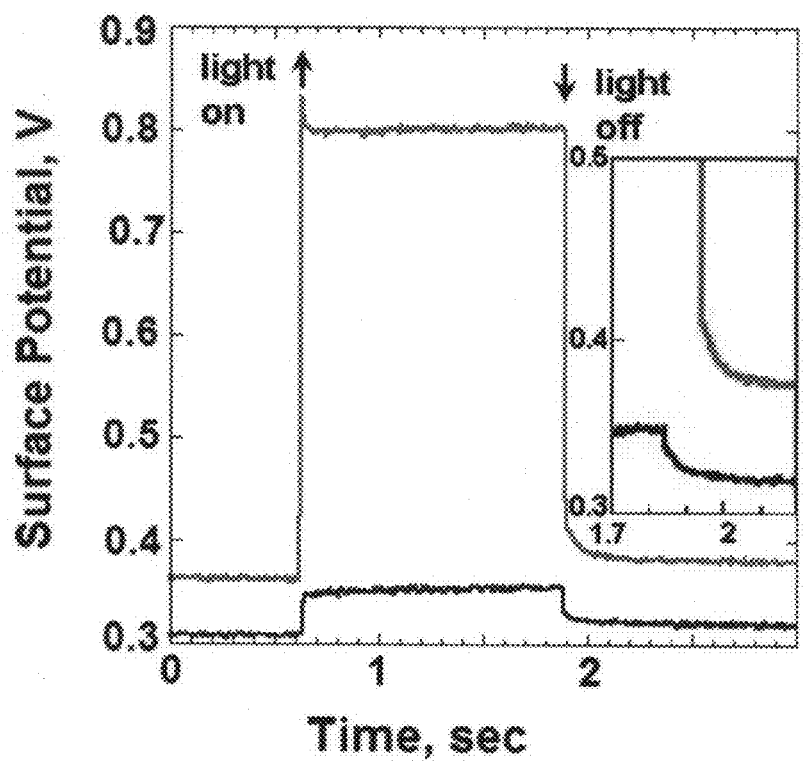
FIG. 4 is a graph of temporal dependence of the PS I-GaAs photoresponse. The red curve corresponds to the photoresponse of n-GaAs crystal coated with PS I, the blue curve to non-coated n-GaAs crystal. The process of photoresponse decay after illumination termination is presented in larger scale. Illumination was provided by a He—Ne laser at 632.8 nm, 5 mW/cm$^2$. The potential sign obtained from the KPFM feedback circuit, is opposite to sign of the measured CPD.
Figure 5:
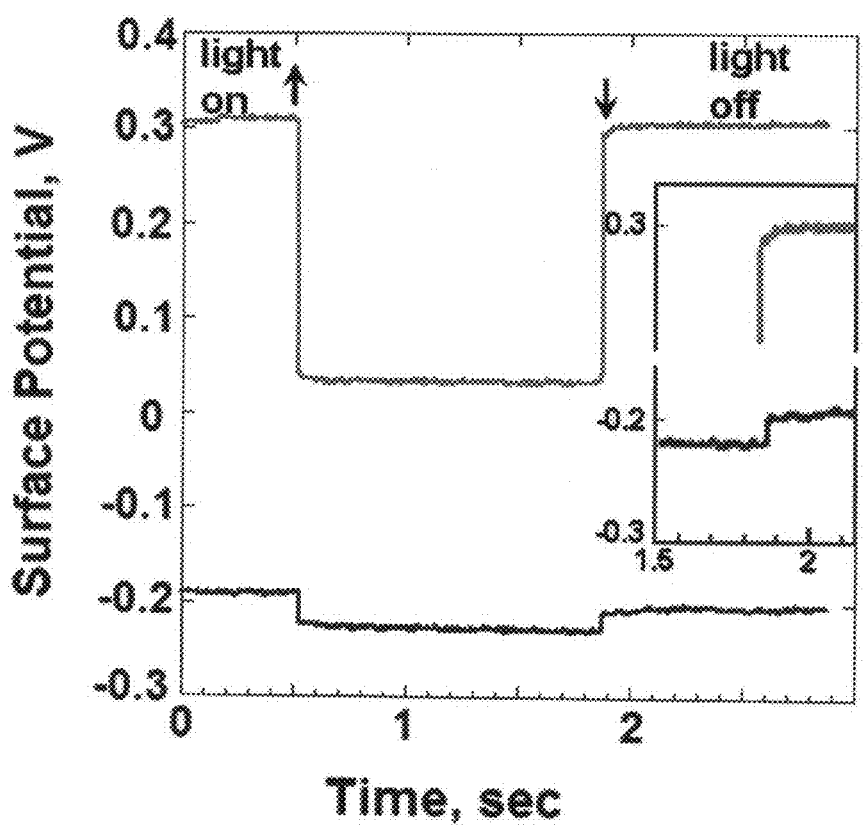
FIG. 5 is a graph of temporal dependence of the PS I-GaAs photoresponse. The red curve corresponds to the photoresponse of p-GaAs crystal coated with PS I, the blue curve to non-coated n-GaAs crystal. The process of photoresponse decay after illumination termination is presented in larger scale. Illumination was provided by a He—Ne laser at 632.8 nm, 5 mW/cm$^2$. The potential sign obtained from the KPFM feedback circuit, is opposite to sign of the measured CPD.

The experimental data of photovoltage formation-decay dynamics are revealed a reversible, light-induced change in the GaAs-PS I monolayer. The onset of steady state was more rapid than the shutter functioning time of 0.7 ms (FIG. 2f, graph lines 1 and 3). The rate of the major component (about 96%) of the total decay of the steady-state photovoltage had a $t_{1/2}$ of unresolved, due to a charge recombination in the PS I attached to the GaAs. As further detailed in the Experimental Procedure section that follows, only about 4% of the decay of the CPD was due to charge recombination in GaAs, with $t_{1/2}$ of 1.5 s (FIG. 2f, curves 2 and 4). Remarkably, the observation that the decay rate of the light-induced steady state CPD in the dry PS I is faster than 0.7 ms which is known to be in the range of the charge recombination rate between P700$^+$ and the reduced iron-sulfur cluster (the final acceptor, FeS) in PS I in aqueous solution. This effect is assumed to be due permanence of behavior of PS I chemisorbed to GaAs in a dry environment.

CONCLUSIONS

The above examples demonstrate that selection of a robust reaction center PS I from cyanobacteria alongside with a rational design of mutations based on the crystallographic structure enables the fabrication of oriented monolayers on the GaAs semiconductor substrate.

Binding of the protein complex to the semiconductor substrate through formation of covalent bond between unique cysteines induced by mutation and a monolayer of connecting small molecules absorbed to the semiconductor surface secures a stable and efficient electronic junction. The dry membrane protein in the monolayer retains its capacity to generate photo-potential of approximately 0.5V. High quantum efficiency makes reaction centers intriguing nano-technological devices for applications in molecular electronics and biotechnology. Formation of oriented multilayers can increase the light absorption cross section and the selectivity of the device to light.

APPENDIX 1

Following are examples of PS I polypeptides together with their source organisms.

| Source Organism | Protein accession number |
| --- | --- |
| *Amphidinium carterae* | CAC34545 |
| *Juniperus chinensis* | CAC87929 |
| *Cedrus libani* | CAC87143 |
| *Spathiphyllum* sp. SM328 | CAC87924 |
| *Persea americana* | CAC87920 |
| *Zamia pumila* | CAC87935 |
| *Ophioglossum petiolatum* | CAC87936 |
| *Taxus brevifolia* | CAC87934 |
| *Afrocarpus gracilior* | CAC87933 |
| *Pinus parviflora* | CAC87932 |
| *Picea spinulosa* | CAC87931 |
| *Phyllocladus trichomanoides* | CAC87930 |
| *Serenoa repens* | CAC87923 |
| *Saururus cernuus* | CAC87922 |
| *Platanus racemosa* | CAC87921 |
| *Pachysandra terminalis* | CAC87919 |
| *Nymphaea* sp. cv. Paul Harriot | CAC87918 |
| *Nuphar lutea* | CAC87917 |
| *Nelumbo nucifera* | CAC87916 |
| *Acer palmatum* | CAD23045 |
| *Cupressus arizonica* | CAC87928 |
| *Cryptomeria japonica* | CAC87927 |
| *Abies alba*] | CAC87926 |
| *Gnetum gnemon* | CAC87925 |
| *Magnolia grandiflora* | CAC87915 |
| *Liquidambar styraciflua* | CAC87914 |
| *Lilium brownii* | CAC87913 |
| *Isomeris arborea* | CAC87912 |
| *Fagus grandifolia* | CAC87911 |
| *Eupomatia laurina* | CAC87910 |
| *Enkianthus chinensis* | CAC87909 |
| *Coptis laciniata* | CAC87908 |
| *Chloranthus spicatus* | CAC87907 |
| *Calycanthus occidentalis* | CAC87906 |
| *Austrobaileya scandens*] | CAC87905 |
| *Amborella trichopoda* | CAC87904 |
| *Acorus calamus* | CAC87142 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An optoelectronic device comprising at least one modified photocatalytic unit, and a surface of a semiconductor material having a linker molecule chemisorbed thereon, wherein said at least one genetically modified photocatalytic unit is covalently attached to said linker molecule such that when light is absorbed by said photocatalytic unit, an electric field is generated at sufficient amount to induce charge carrier locomotion within said semiconductor material.

2. The device of claim 1, being operative, in dry environment.

3. The device of claim 1, wherein said at least one modified photocatalytic unit comprises at least one modified polypeptide having an amino acid sequence of a polypeptide of a photocatalytic unit of a photosynthetic organism.

4. The device of claim 3, wherein said photosynthetic organism is a green plant.

5. The device of claim 3, wherein said photosynthetic organism is a cyanobacteria.

6. The device of claim 5, wherein said photocatalytic unit is a *Synechosystis* sp. PCC 6803 photocatalytic unit.

7. The device of claim 3, wherein said photocatalytic unit is PS-1.

8. The device of claim 3, wherein said amino acid sequence of said polypeptide of said photocatalytic unit comprises at least one substitution mutation.

9. The device of claim 8, wherein said substitution mutation is on an extra-membrane loop of said photocatalytic unit.

10. The device of claim 8, wherein said at least one substitution mutation is cysteine.

11. The device of claim 3, wherein said amino acid sequence of said polypeptide is psaB.

12. The device of claim 11, wherein said Psa B comprises a substitution mutation in at least one position demarked by the coordinates D235C/Y634C.

13. The device of claim 11, wherein said Psa C comprises a substitution mutation in at least one position demarked by the coordinates W31C.

14. The device of claim 3, wherein said amino acid sequence of said polypeptide is psaC.

15. The device of claim 1, wherein said surface is made of a semiconductor selected from the group consisting of an n-type semiconductor, a p-type semiconductor and an i-type semiconductor.

16. The device of claim 1, wherein said at least one modified photocatalytic unit is a plurality of modified photocatalytic unit orientated at a substantially similar direction with respect to said surface.

17. The device of claim 1, serving as a component in a device selected from the group consisting of a photodiode, a phototransistor, a logic gate, a field effect transistor, an optocoupler, a photodetector, an optical switch and an image sensor.

18. A field effect transistor device, comprising a semiconductor source layer, a semiconductor drain layer, a semiconductor channel layer having linker molecules chemisorbed thereon, and at least one layer of genetically modified photocatalytic units covalently attached to said linker molecules in a manner such that when light is absorbed by said at least one photocatalytic unit, an electric field is generated at sufficient amount to induce charge carrier locomotion between said source and said drain through said channel.

19. The device of claim 18, wherein said modified photocatalytic units are arranged layerwise and orientated at a substantially similar direction with respect to said surface.

20. The device of claim 18, being operative in dry environment.

21. The device of claim 18, wherein said at least one modified photocatalytic unit comprises at least one modified polypeptide having an amino acid sequence of a polypeptide of a photocatalytic unit of a photosynthetic organism.

* * * * *